United States Patent
Fürstner et al.

(12) 
(10) Patent No.: US 6,348,551 B1
(45) Date of Patent: Feb. 19, 2002

(54) SELECTIVE OLEFIN METATHESIS OF BIFUNCTIONAL OR POLYFUNCTIONAL SUBSTRATES IN COMPRESSED CARBON DIOXIDE AS REACTION MEDIUM

(75) Inventors: Alois Fürstner; Walter Leitner, both of Mülheim an der Ruhr; Daniel Koch, Duisburg; Klaus Langemann, Worms; Christian Six, Neuss, all of (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/403,331

(22) PCT Filed: Apr. 4, 1998

(86) PCT No.: PCT/EP98/01977

§ 371 Date: Oct. 15, 1999

§ 102(e) Date: Oct. 15, 1999

(87) PCT Pub. No.: WO98/47891

PCT Pub. Date: Oct. 29, 1998

(30) Foreign Application Priority Data

Apr. 18, 1997 (DE) .......................................... 197 16 231
May 16, 1997 (DE) .......................................... 197 20 798

(51) Int. Cl.$^7$ ................................................. C08F 4/72
(52) U.S. Cl. ....................... 526/171; 526/170; 526/172; 526/266; 526/308
(58) Field of Search ............................... 526/170, 171, 526/172, 266, 308

(56) References Cited

U.S. PATENT DOCUMENTS 5,936,100 A 8/1999 Furstner et al. ............. 549/266

FOREIGN PATENT DOCUMENTS

WO 91 14665 10/1991
WO WO 96/32421 * 10/1996

OTHER PUBLICATIONS

A. Furstner, et al. "Conformationally Unbiased . . . Metathesis", Journal of Organica Chemistry, Bd. 61, 1996, pp. 3942–3943.*
Morrison et al. "Organic Chemistry", 3rd Edition, Allyn and Bacon, Inc., 1973, Chapter 9, p. 292.*
V. Dragutan, et al.: "Olefin Metathesis and . . . Cyclo–olefins", 1985, J. Wiley, p. 68.
P. Bertinato, et al. "Studies Toward a Synthesis . . . Chemistry", Bd. 61, 1996, pp. 8000–8001.
A. Fürstner, et al. "Conformationally Unbiased . . . Metathesis", Journal of Organic Chemistry, Bd. 61, 1996, pp. 3942–3943.
K.C. Nicolaou et al.: "An approach to Epothilones . . . Metathesis", Angewandte Chemie. International Edition Bd. 35, Nr. 20, 1996, pp. 2399–2401.
O. Reiser, Topics in Catalysis, 5: 105–112 (1998).

* cited by examiner

Primary Examiner—David W. Wu
Assistant Examiner—William Cheung
(74) Attorney, Agent, or Firm—Norris McLaughlin & Marcus

(57) ABSTRACT

Cyclic products are prepared by selective olefin metathesis of bifunctional or polyfunctional substrates in the presence of one or several homogeneous or heterogeneous metathesis catalysts in a reaction medium. The invention is characterized in that the substrates contain two or more functional groups in the form of substituted or non-substituted alkene or alkyne units and in that the reaction medium essentially consists of compressed carbon dioxide. Also disclosed is the preparation of cyclic or polymer products according to the disclosed process, the reaction temperature and total pressure being matched to ensure that the density of the reaction medium lies in a range $d=0.2–1.5$ g·cm$^{-3}$ and that the product distribution is essentially controlled by the reaction medium density.

29 Claims, 1 Drawing Sheet

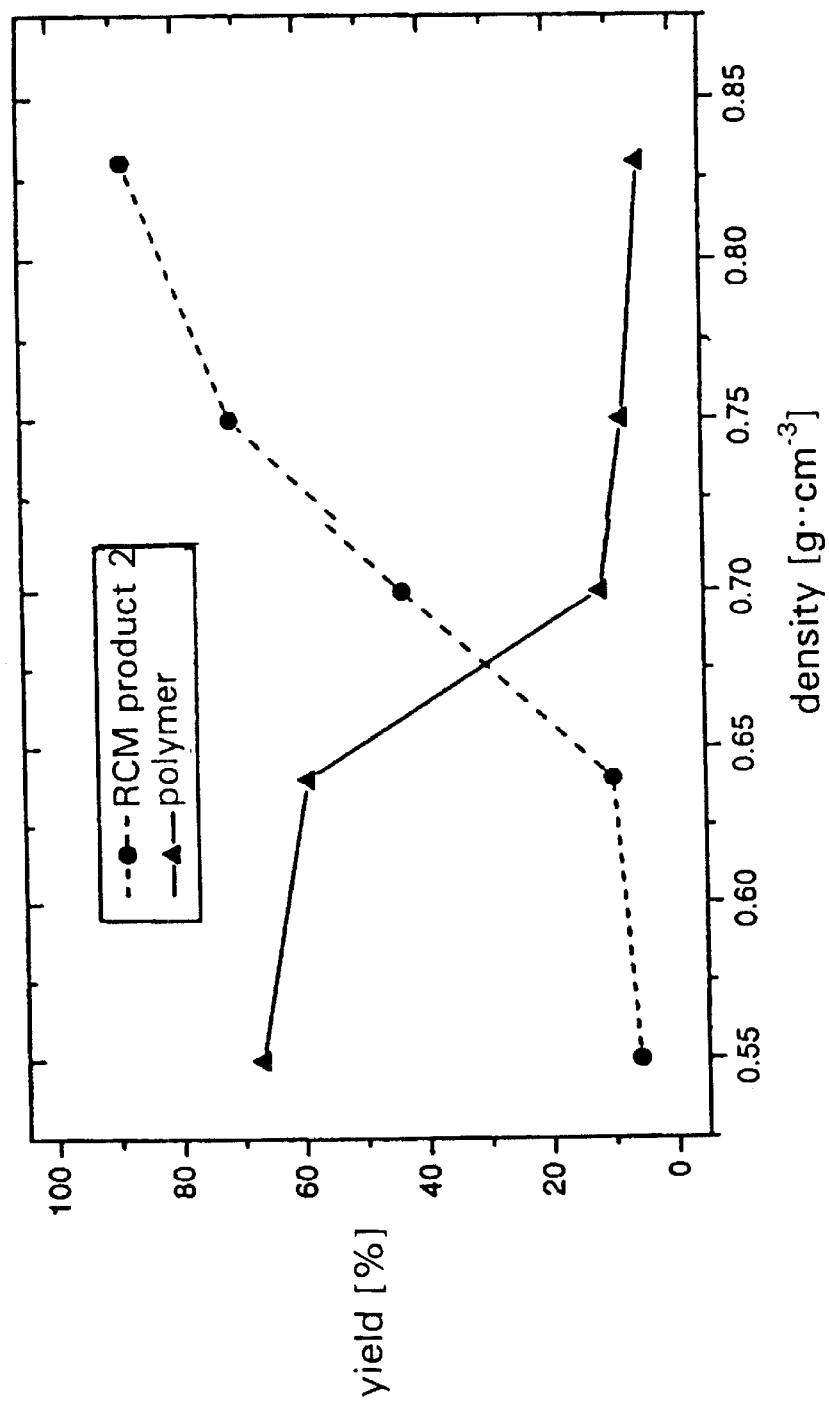
Figure 1: Selective olefin metathesis of 1 in compressed carbon dioxide at different densities of the reaction medium.

SELECTIVE OLEFIN METATHESIS OF BIFUNCTIONAL OR POLYFUNCTIONAL SUBSTRATES IN COMPRESSED CARBON DIOXIDE AS REACTION MEDIUM

This application is a 371 of PCT/EP98/01977, which was filed on Apr. 4, 1998.

The present invention relates to the preparation of cyclic products by selective olefin metathesis of bifunctional or polyfunctional substrates in the presence of one or more homogeneous or heterogeneous metathesis catalysts in a reaction medium, characterized in that the substrates contain two or more functional groups in the form of substituted or unsubstituted alkene or alkyne moieties, and the reaction medium essentially consists of compressed carbon dioxide. The invention further relates to the preparation of cyclic or polymeric products by the process mentioned wherein the reaction temperature and the total pressure are mutually adjusted in such a way that the density of the reaction medium is within a range of $d=0.2–1.5$ g·cm$^{-3}$, and the product distribution is essentially controlled by the density of the reaction medium. "Olefin metathesis" means the mutual transalkylideneation of alkenes. Reactions of this kind are usually catalyzed by metallic compounds (review: Ivin, K. J.; Mol, J. C., Olefin Metathesis and Metathesis Polymerization, Academic Press, New York, 1997) and find applications in a wide variety of technically important processes. These include the preparation of alkenes, for example, in the Shell higher olefin process (Sherwood, M., Chem. Ind. (London) 1982, 994), in the Phillips triolefin process, and in the production of α,ω-diolefins (Banks, R. L. et al., J. Mol. Catal. 1982, 15, 21). Another application is the ring-opening oligomerization or polymerization of cycloalkenes (ROMP, U.S. Pat. No. 4,567,244) which is used, for example, for the production of Vestenamer® (Dräxler, A., Der Lichtbogen 1986, 35, 24) or Norsorex® (Ohin, R. F., Chemtech 1980, 198). Further, there may be mentioned the oligomerization or polymerization of acyclic dienes (ADMET, Lindmark-Hamberg, M. et al., Macromolecules 1987, 20, 2951), the synthesis of carbo- and heterocycles having different ring sizes by ring-closure metathesis (RCM, WO 96/04289, Grubbs, R. H. et al., Acc. Chem. Res. 1995, 28, 446), crossed metatheses of different alkenes (Brümmer, O. et al., Chem. Eur. J. 1997, 3, 441), and ene-yne metatheses (Kinoshita, A. et al., Synlett 1994, 1020; Kim, S.-H. et al., J. Org. Chem. 1996, 61, 1073). Various carbo- or heterocycles having ring sizes of ≧5 prepared by RCM have already been used for the synthesis of natural or synthetic active substances, odoriferous substances and flavors, pheromones, pharmaceuticals, crown ethers etc. (U.S. patent application Ser. No. 08/767.561 of Dec. 16, 1996, Studiengesellschaft Kohle mbH). There may be mentioned, in particular, the efficient synthesis of macrocycles by RCM (Fürstner, A. et al., J. Org. Chem. 1996, 61, 3942), which is the basis, inter alia, of several syntheses of the antitumor drug epothilone and its analogues (Bertinato, P. et al., J. Org. Chem. 1996, 61, 8000; Nicolaou, K. C. et al., Angew. Chem. 1996, 108, 2554; Yang, Z. et al., Angew. Chem. 1997, 109, 170; Schinzer, D. et al., Angew. Chem. 1997, 109, 543).

The preparation of cyclic compounds from open-chain substrates is a central problem of chemical synthesis. Cyclizations are often performed in an intramolecular ring-closure reaction, proceeding from bifunctional or polyfunctional precursors. The desired ring-closure reactions are always competing with a polymerization of the substrates ("polymers" in this connection means products formed by the linkage of two or more substrate molecules, including, in particular, dimers and oligomers of low molecular weights). This general problem also applies to the preparation of cyclic products by olefin metatheses. If this reaction is performed with bifunctional or polyfunctional substrates in which the mentioned functional groups are alkenes or alkynes, mixtures of the cyclization product and polymers are formed. In Scheme 1, this competition situation is exemplified by the metathesis reaction of the diene 1.

Scheme 1:
Competition between cyclization and polymerzation in the olefin metathesisof bifunctional or polyfunctional substrates as exemplified by diene 1.

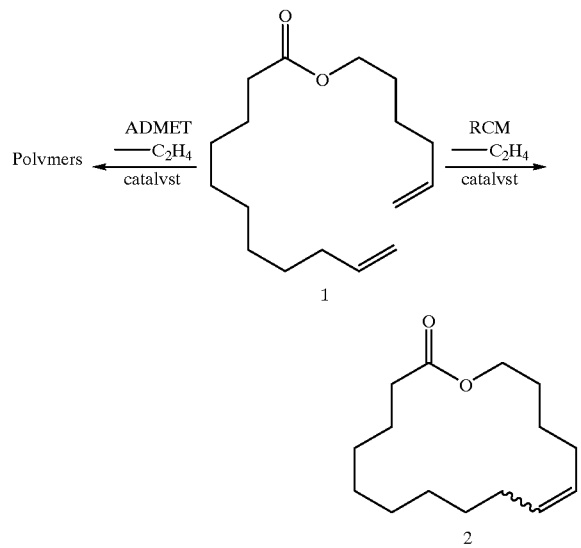

In detail, the product distribution between the polymer and the cyclization product depends on the structure of the substrates, the catalyst used and the reaction conditions. The formation of the cyclization product is favored by performing the reaction in an organic solvent at a high dilution. This applies, in particular, to the preparation of medium-sized (8–11 ring members) and large-sized (≧12 ring members) rings. In general, hydrocarbons (hexane, toluene, xylene, cumene etc.) or chlorinated hydrocarbons (dichloromethane, 1,2-dichloroethane, halobenzenes etc.) are preferred as solvents for olefin metatheses. The large reaction volumes and expensive dosage methods required for achieving the necessary high dilutions limit the maximum yields obtainable per space and time. The separation of the products present in high dilutions from the reaction mixtures further requires time- and energy-consuming separation operations, such as chromatography, rectification or distillation. The thermal stress in distillative separations may adversely affect the quality of the products obtained and often leads to an irreversible deactivation of the catalysts employed. In the synthesis of physiologically active compounds, residual solvents which may not be toxicologically safe represent a particular problem. Also with respect to possible environmental impacts, the use of large amounts of solvents involves drawbacks in terms of process technology. Therefore, methods resulting in a complete or partial elimination of the mentioned solvents are of great technical importance.

Carbon dioxide has been proposed as an ecologically safe reaction medium for metal-catalyzed reactions [reviews: Jessop, P. G. et al., Science 1995, 269, 1065; Morgenstern, D. A. et al. in: Green Chemistry (Ed.: P. T.

Anastas, T. C. Williamson) ACS *Symp. Ser.* 262, American Chemical Society, Washington D.C., 1996, p. 132 et seq.; Dinjus, E. et al. in: *Chemistry under Extreme or Non-Classical Conditions* (Ed.: R. van Eldik, C. D. Hubbard), Wiley, New York, 1996, p. 219 et seq.]. Metathesis reactions in compressed (gaseous, liquid or supercritical) carbon dioxide are described in WO 96/32421; however, this includes only ring-opening polymerization (ROMP) reactions of cyclic monofunctional alkenes as substrates. We now describe a process for the preparation of chemical products by selective olefin metathesis of bifunctional or polyfunctional substrates in the presence of a homogeneous or heterogeneous metathesis catalyst in a reaction medium, characterized in that the substrates contain two or more functional groups in the form of substituted or unsubstituted alkene or alkyne moieties, and the reaction medium essentially consists of compressed (gaseous, liquid or supercritical) carbon dioxide. In particular, the present invention relates to the preparation of cyclic compounds having ring sizes of $n \geq 5$ by the ring-closure metathesis of bifunctional or polyfunctional substrates. Surprisingly, it has been found that cyclic or polymeric products can be selectively obtained with a high selectivity by varying the density of the reaction medium.

Using the present invention, carbo- and heterocycles of arbitrary ring size n ($n \geq 5$) including medium-sized (n=8–11) and large-sized ($n \geq 12$) rings can be prepared. The solvents used to date in such reactions, which are in part physiologically doubtful and environmentally harmful (e.g., aromatics or chlorinated hydrocarbons), are thus completely or substantially replaced by a nontoxic, noncombustible, inexpensive reusable reaction medium. Performing the reaction in compressed carbon dioxide has the further consequence that substituents at the substrates are tolerated which are not compatible with the olefin metathesis in conventional solvents. Further, the processing of the reaction mixtures is substantially simplified due to the special solvent properties of compressed carbon dioxide, for example, by segregating the products wholly or partially from the reaction mixture, or by separating them wholly or partially from the catalyst using the extractive properties of compressed $CO_2$ (K. Zosel, *Angew. Chem.* 1978, 90, 748). After separation of the products, the remaining catalysts are in part reusable for olefin metatheses.

The reaction temperature and the total pressure can be freely chosen within broad ranges in the selective olefin metathesis of bifunctional or polyfunctional substrates in compressed carbon dioxide, but they are mutually adjusted in such a way that the density of the reaction medium is within a range of $d=0.2-1.5$ g·cm$^{-3}$. Preferred reaction temperatures are within a range of from 250 to 400 K, particularly preferred within a range of from 280 to 345 K. Preferred total pressures are within a range of from 30 to 300 bar, particularly preferred within a range of from 50 to 220 bar. The ring-closure reaction of the bifunctional or polyfunctional substrate is favored by applying high densities while polymerization preferentially proceeds in the range of low densities. The respectively optimum range of densities depends on the structure of the substrate and on the catalyst used.

According to the present invention, the ring-closure reaction is preferably performed at densities $d=0.4-1.5$ g·cm$^{-3}$, more preferably at densities $d=0.6-1.5$ g·cm$^{-3}$. High densities are preferred, in particular, for the preparation of medium-sized and large-sized rings (for the metathesis of diene 1 to lactone 2 as a specific example, see FIG. 1), while the chosen density is less critical for the preparation of rings with n=5–7. Particularly preferred conditions for the ring-closure reaction can be seen from the appended Examples, which are not intended, however, to limit the applicability of the present invention in any way.

BRIEF DESCRIPTION OF FIGURES

In contrast to cyclization, the polymerization by the metathesis of a bifunctional or polyfunctional substrate is preferably performed at low densities $d=0.2-0.65$ g·cm$^{-3}$ of the reaction medium which essentially consists of compressed carbon dioxide. As for the RCM, the optimum range of densities depends on the substrate and catalyst employed. For the metathesis with polymerization of diene 1 as a specific example, see FIG. 1.

As the catalysts or catalyst precursors, any metathesis-active metallic compound can be used in the present invention, irrespective of whether they are homogeneous or heterogeneous in the reaction medium as long as they are not inactivated by compressed carbon dioxide. The catalysts can be employed in isolated form or produced in situ in the reaction medium from suitable precursors. The amount of catalyst employed is not critical, preferred amounts of catalyst being within a range of from 0.01 to 10 mole percent, based on the substrate used. Preferred catalysts or catalyst precursors are transition metal-carbenes, or transition metallic compounds which form metal-carbenes under the reaction conditions, or transition metal salts in connection with an alkylating agent. These include, inter alia, systems of general types I–IX (references: type I (M=Ru, Os): WO 96/04289, Feb. 15, 1996; Nguyen et al., *J. Am. Chem. Soc.* 1992, 114, 3974; Nguyen et al., *J. Am. Chem. Soc.* 1993, 115, 9858; Schwab, P. et al., *Angew. Chem.* 1995, 107, 2179; Schwab, P. et al., *J. Am. Chem. Soc.* 1996, 118, 100; Mohr, B. et al., *Organometallics* 1996, 15, 4317; type II (M=Mo, W): Schrock, R. R. et al., *J. Am. Chem. Soc.* 1990, 112, 3875; Fujimura, O. et al., *Organometallics* 1996, 15, 1865; type III: Quingnard, F. et al., *J. Mol. Catal.* 1986, 36, 13; type IV (M=Nb, Ta): Rocklage, S. M. et al., *J. Am. Chem. Soc.* 1981, 103, 1440; Wallace, K. C. et al., *Macromolecules* 1987, 20, 448; type V (cp=substituted or unsubstituted cyclopentadienyl) : U. S. 4,567,244, Jan. 28, 1986; type VI: Herrmann, W. A. et al., *Angew. Chem.* 1991, 103, 1704; type VII: Nugent, W. A. et al., *J. Am. Chem. Soc.* 1995, 117, 8992; type VIII: Davie, E. S., *J. Catal.* 1972, 24, 272; type IX: Herrmann, W. A. et al., *Angew. Chem.* 1996, 108, 1169.).

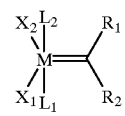

I

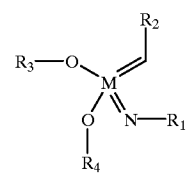

II

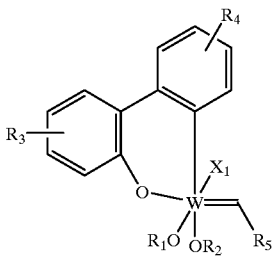

III

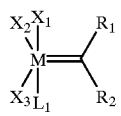

IV

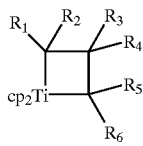

V $R_1$—$ReO_3$

VI $WO(X_1)_2(OR_1)_2/PbEt_4$

VII $Mo(CO)_6/Al_2O_3$

VIII

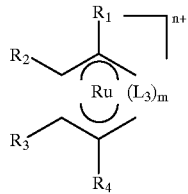

IX $R_1$–$R_6$ are residues which are independently selected from hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsufinyl; each of which may optionally be substituted with $C_1$–$C_{12}$ alkyl, $C_1$–$C_{12}$ perfluoroalkyl, halogen, $C_1$–$C_5$ alkoxy or aryl. In cyclic compounds, the residues $R_1$–$R_{10}$ can be linked to one another.

$X_1$–$X_3$ are arbitrarily defined anionic ligands which are independently selected, especially from $F^-$, $Cl^-$, $Br^-$, $I^-$, $CN^-$, $SCN^-$, $R_1O^-$, $R_1R_2N^-$, $(R_1$–$R_5)$-allyl$^-$, $(R_1$–$R_5)$-cyclopentadienyl$^-$, the residues $R_1$–$R_5$ corresponding to the above definition.

$L_1$–$L_3$ are neutral ligands which are independently selected, especially from CO, $CO_2$, $R_1NCO$, $R_1R_2C=CR_3R_4$, $R_1C\equiv CR_2$, $R_1R_2C=NR_3$, $R_1C\equiv N$, $R_1OR_2$, $R_1SR_2$, $NR_1R_2R_3$, $PR_1R_2R_3$, $AsR_1R_2R_3$, residues $R_1$–$R_4$ corresponding to the above definition.

m, n are integers of from 0 to 6. Particularly preferred catalysts or catalyst precursors are carbene complexes of general type I with $L_1$–$L_2$=$PR_1R_2R_3$, $R_1$–$R_3$ corresponding to the above definition, particularly preferred residues $R_1$–$R_3$ being aryl or alkyl, especially secondary alkyl or cycloalkyl residues. Also particularly preferred are carbene complexes of general type II with $R_1$=aryl and $R_2$–$R_4$= $C_1$–$C_{20}$ alkyl, each of which may optionally be substituted with $C_1$–$C_{12}$ alkyl, $C_1$–$C_{12}$ perfluoroalkyl, aryl, halogen.

Reactions according to the present invention may also be performed in the presence of one or more additives which may result in, for example, an easier handling of the substrates or catalysts, or an improvement of the solvent properties of the reaction medium, or an increase of the reaction rate, or an improvement of the yield. For example, such additives may be independently selected from: water, phosphorus compounds, amines, perfluorinated compounds (see Patent Application Studiengesellschaft Kohle m.b.H. DE 197 02 025.9, Jan. 23, 1997), Lewis-acidic compounds, metal alkoxides, organic solvents (e.g., dichloromethane, trichloromethane, tetrachloro-methane, 1,2-dichloroethane, trichloroethene, benzene, toluene, xylene, cumene, hexane, cyclohexane, halobenzenes, tetrahydrofuran, tert-butyl methyl ether, diethyl ether, dimethoxy-ethane, dimethylformamide, ethyl acetoacetate, acetone, dimethyl carbonate, alcohols).

In the present invention, "bifunctional or polyfunctional substrates" means any chemical compound which contains two or more functional groups in the form of substituted or unsubstituted alkene or alkyne moieties allowing metathesis reaction. The substrates may be either conformationally preorganized or completely flexible. In addition to the functional groups mentioned which participate in the reaction, the substrates may contain any number of further groups or heteroatoms which are compatible with the metathesis reaction. These include, inter alia, branched or unbranched alkyl residues, aromatic or non-aromatic carbocyclic rings, carboxylic acids, esters, ethers, epoxides, silyl ethers, thioethers, thioacetals, anhydrides, imines, silyl enol ethers, ammonium salts, amides, nitrites, perfluoroalkyl groups, gem-dialkyl groups, alkynes, alkenes, halogens, alcohols, ketones, aldehydes, carbamates, carbonates, urethanes, sulfonates, sulfones, sulfonamides, nitro groups, organosilane units, metal centers, oxygen-, nitrogen-, sulfur-, phosphorus-containing heterocycles. Mixtures of substrates according to the present invention may also be reacted; in this case, the substrates may be supplied to the reaction medium in admixture or sequentially. The substrates may also be in supported form.

In particular, selective olefin metatheses in compressed carbon dioxide may also be performed with bifunctional or polyfunctional substrates which contain one or more primary, secondary or tertiary basic amine units which can lead to a deactivation of the metathesis catalysts in conventional solvents.

By the selective olefin metathesis of bifunctional or poly-functional substrates in compressed carbon dioxide, there may be obtained, in particular, macrocyclic esters, ethers, amines and ketones which may be used, for example, as odoriferous substances and their precursors. The range of applications includes, inter alia, that of RCM in organic solvents (see, inter alia, U.S. patent application Ser. No. 08/767.561 of Dec. 16, 1996, Studiengesellschaft Kohle mbH). This includes, for example, the macrocyclic esters 2 and 4 and double bond-related isomers thereof (e.g., from substrates 1 and 3), which themselves have a distinct musk-like smell and are converted to the known perfume ingredients pentadecanolide and Arova 16®, respectively, by hydrogenation.

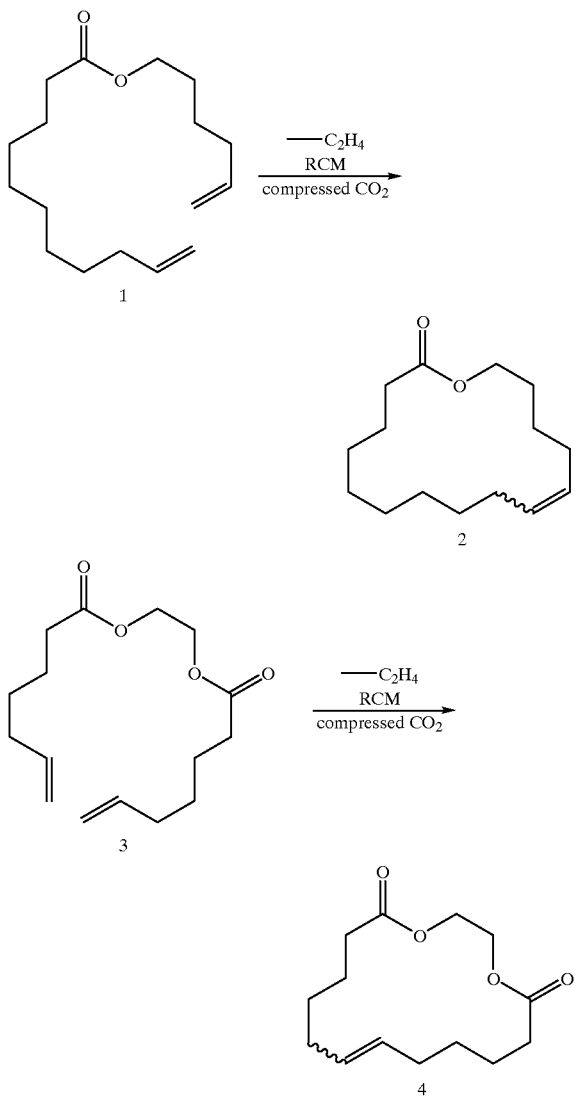

The range of application of the selective olefin metathesis of bifunctional or polyfunctional substrates in compressed carbon dioxide further comprises a series of homologous substituted or unsubstituted cyclic ketones having ring sizes of from 12 to 30 including cibetone, muscone, Exalton® and Muscenon® (review: Ohloff, G., Riechstoffe und Geruchssinn, Springer, Berlin, 1990; Bauer K. et al., *Ullmann's Encyclopedia of Industrial Chemistry*, VCH, Weinheim, 5th Ed., 1988, Vol. A11, 141). The antitumor drug epothilone and its analogues can also be prepared using this reaction principle (Bertinato, P. et al., *J. Org. Chem.* 1996, 61, 8000; Nicolaou, K. C. et al., *Angew. Chem.* 1996, 108, 2554; Yang, Z. et al., *Angew. Chem.* 1997, 109, 170; Schinzer, D. et al., *Angew. Chem.* 1997, 109, 543).

The compounds prepared by selective olefin metathesis of bifunctional or polyfunctional substrates in compressed carbon dioxide are wholly or partially separated from the catalyst when the pressure is released from the reactor, and can be collected in suitable receivers. The carbon dioxide released when the products are isolated can again be employed for charging or flushing the reactor. Further, the catalyst thus separated from the product can be reused for metathesis reactions.

In integrated processes, selective olefin metatheses of bifunctional or polyfunctional substrates in compressed carbon dioxide may also be followed by further reactions in compressed carbon dioxide, such as carbon-carbon bond formation, reduction or oxidation for the further functionalization of the products obtained. In particular, by selective olefin metathesis and subsequent hydrogenation in compressed carbon dioxide as the reaction medium, saturated macrocyclic musk scents, such as Exaltolid®, Arova 16® and Exalton®, can be directly obtained from suitable acyclic unsaturated precursors in an integrated process.

By selective olefin metathesis of bifunctional or polyfunctional substrates in compressed carbon dioxide, unsaturated polymers, such as polymeric hydrocarbons, polyesters, polyamides, polycarbonates, polyurethanes and the like, can be prepared. These are of economical importance, e.g., as thermoplastics, elastomers, fillers, insulation materials, adsorbers and in the preparation of optical devices and as additives in vulcanization.

The polymers obtained from the reaction mixture can be further purified and processed using customary methods. Further reactions of the polymers, such as hydrogenation or oxidation, as well as known methods of polymer processing in compressed carbon dioxide [Schmeder, H. in: *Chemistry under Extreme or Non-Classical Conditions* (Ed.: R. van Eldik, C. D. Hubbard), Wiley, New York, 1996, p. 280 et seq.] can be applied within the scope of integrated processes. The carbon dioxide liberated when the pressure is released can again be compressed and used as a reaction medium.

The following Examples describe prototypical metathesis reactions in compressed carbon dioxide under preferred conditions without in any way limiting the scope, range of application or any advantages of the present invention. The abbreviation Cy represents cyclohexyl (cyclo-$C_6H_{11}$), d represents the density, and cat. means catalyst.

EXAMPLE 1
Preparation of oxacyclohexadec-11-ene-2-one (2)

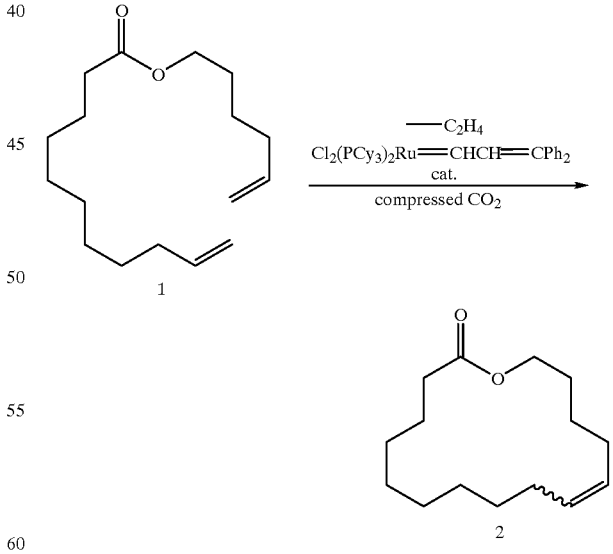

Diene 1 (180 mg) and trans-$[Cl_2(PCy_3)_2Ru=CHCH=CPh_2]$ (7 mg) were charged in a stainless steel high-pressure reactor (V=225 $cm^{-3}$) under argon atmosphere. The reactor was filled with 170 g of $CO_2$ using a compressor (d=0.76 g·$cm^{-3}$), and the reaction mixture was stirred at 313 K for 72 h. Then, the $CO_2$ pressure was released over a cooling trap cooled at 233 K. For completely removing the product from the reactor, the reactor was flushed twice with 170 g of $CO_2$ each, followed by releasing the pressure over the cooled cooling trap. After warming up, 157 mg of a colorless oil which, according to GC analysis, consisted of 71% compound 2 as a mixture of the double bond-related isomers (cis:trans=26:74) and 21% unreacted 1 was obtained from the cooling trap.

$^1$H NMR (200 MHz, $CDCl_3$) δ5.45–5.28 (m, 2H), 4.18–4.07 (m, 2H), 2.37–2.29 (m, 2H), 2.10–2.00 (m, 4H), 1.72–1.54 (m, 4H), 1.49–1.30 (m, 10H); IR (film) 3000, 2928, 2856, 1736, 1461, 1385, 1346, 1252, 1234, 1168, 1152, 1113, 1085, 1024, 969, 719 $cm^{-3}$.

EXAMPLE 2

Selective Olefin Metathesis of Alkene (1) for the Preparation of (2) or of Polymers at Different Densities of the Reaction Mixture Diene 1 (180 mg) and trans-$[Cl_2(PCy_3)_2Ru=CHCH=CPh_2]$ (7 mg) were charged in a stainless steel high-pressure reactor (V=225 $cm^{-3}$) under argon atmosphere. The reactor was filled with the desired amount of $CO_2$ using a compressor, and the reaction mixture was stirred at 313 K for 72 h. Then, the $CO_2$ pressure was released over a cooling trap cooled at 233 K, and the reactor was washed with acetone. The combined fractions were concentrated to dryness, and the low-molecular weight components (unreacted 1 and cyclization product 2) were separated from the oligomers by chromatography on silica gel using hexane/ethyl acetate as the eluent. The proportions of 1 and 2 were determined by GC analysis. The results are summarized in Table 1 and graphically represented in FIG. 1.

TABLE 1

Selective olefin metathesis of 1 in compressed carbon dioxide at different densities of the reaction medium

| Example | $CO_2$ [g] | d [g · $cm^{-3}$] | 2 [%] | polymer [%] | 1 [a] [%] |
|---|---|---|---|---|---|
| 2a | 186 | 0.83 | 88.3 | 5 | 9 |
| 2b | 170 | 0.76 | 71.1 | 8 | 21 |
| 2c | 157 | 0.70 | 43.5 | 12 | 44 |
| 2d | 145 | 0.64 | 10 | 59 | 31 |
| 2e | 124 | 0.55 | 6 | 67 | 27 |

[a]unreacted substrate after completion of the reaction.

EXAMPLE 3

Preparation of 1,4-dioxacyclohexadec-10-ene-5,16-dione (4) and Reusability of the Catalyst

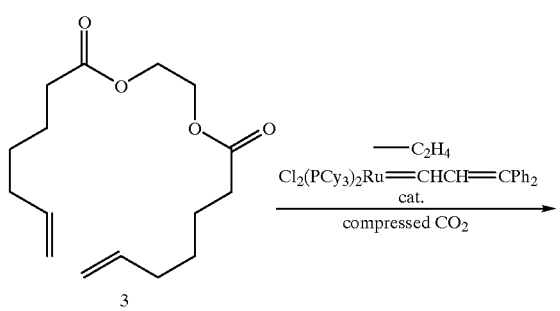

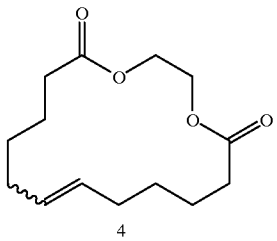

4

The unsaturated ester 3 (180 mg) and trans-$[Cl_2(PCy_3)_2Ru=CH—CH=CPh_2]$ (14 mg) were charged in a stainless steel high-pressure reactor (V=225 $cm^{-3}$) under argon atmosphere. The reactor was filled with 140 g of $CO_2$ using a compressor (d=0.62 g·$cm^{-3}$), and the reaction mixture produced was stirred at 313 K for 72 h. The $CO_2$ pressure was released over a cooling trap cooled at 233 K. After warming up, 160 mg of a colorless oil which, according to GC analysis, consisted of 30.4% compound 4 was obtained from the cooling trap.

The residue remaining in the reactor was again charged with 3 (170 mg) and $CO_2$ (140 g) (d=0.62 g $cm^{-3}$) and stirred at 313 K for 170 h. After releasing the pressure as described above, the cooling trap and the reactor were washed with $CH_2Cl_2$, and the combined washings were concentrated to obtain 160 mg of a colorless oil which, according to GC, consisted of 70.4% 4. The crude product obtained was purified by column chromatography. Compound 4 was obtained in the form of colorless crystals.

Yield: 102 mg (67%)

m.p. 46–47° C.; $^1$H NMR (200 MHz, $CDCl_3$) δ5.39–5.21 (m, 2H), 4.30 (s, 1H), 4.27 (s, 3H), 2.37–2.26 (m, 4H), 2.11–2.02 (m, 4H), 1.71–1.55 (m, 4H), 1.48–1.38 (m, 4H); IR (KBr) 2931, 2854, 1733, 1462, 1439, 1398, 1371, 1296, 1275, 1257, 1223, 1169, 1102, 1072, 1035, 965, 874 $cm^{-1}$.

EXAMPLE 4

Preparation of 2,2,5-trimethylcyclo-4-heptenone (6)

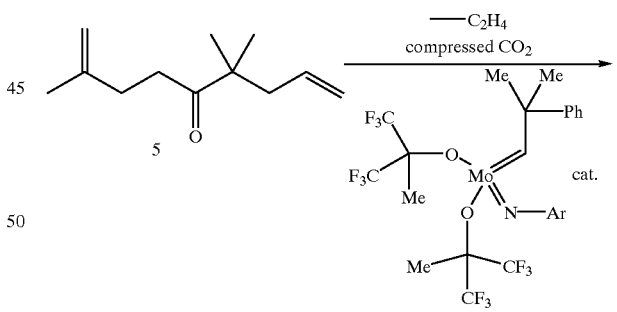

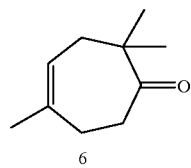

6

Dienone 5 (222 mg) and $[\{(CF_3)_2MeCO\}_2Mo(=CHCMe_2Ph)(=NC_6H_3\text{-}i\text{-}Pr_2\text{-}2,6)]$ (46 mg) were charged in a stainless steel high-pressure reactor (V=225 $cm^3$) under argon atmosphere. The reactor was filled with 170 g of $CO_2$ (d=0.76 g·$cm^{-3}$) using a compressor, and the resulting reaction mixture was stirred at 313 K. After 72 h, the CO$_2$ pressure was released over a cooling trap cooled at 233 K. The reactor and the cooling trap were washed with acetone, the combined washings were concentrated, and the residue was purified by column chromatography (silica gel, hexane/ethyl acetate 12:1). The product 6 (117 mg, 62%) and unreacted 5 (56 mg, 25 mg) were obtained as colorless oils.

EXAMPLE 5
Preparation of 3,3'-bis-2,5-dihydrofuranyl (8)

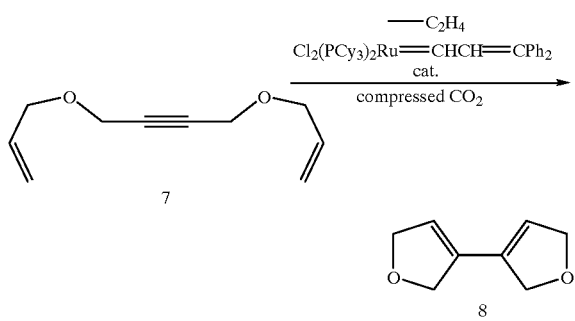

The unsaturated ester 7 (187 mg) and trans-[Cl$_2$(PCy$_3$)$_2$Ru=CH—CH=CPh$_2$] (19 mg) were charged in a stainless steel high-pressure reactor (V=225 cm$^{-3}$) under argon atmosphere. The reactor was filled with 169 g of CO$_2$ using a compressor (d=0.75 g·cm$^{-3}$) and the reaction mixture was stirred at 313 K for 48 h. Then, the CO$_2$ pressure was released over a cooling trap cooled at 233 K, and the reactor was washed with acetone. The combined fractions were concentrated to dryness, and silica gel chromatography with hexane/ethyl acetate (10:1) yielded pure 8 (97 mg, 62%) as a colorless solid.

EXAMPLE 6
Preparation of 1-(toluene-4-sulfonyl)-2,5-dihydro-1H-pyrrole (10)

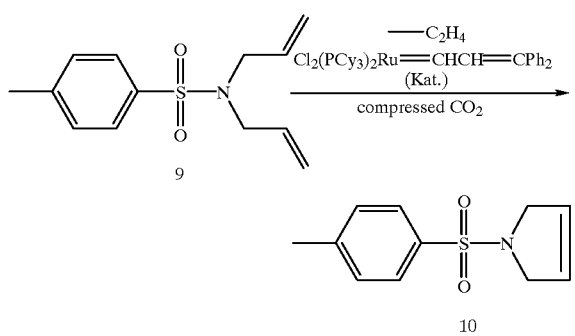

Diene 9 (219 mg) and trans-[Cl$_2$(PCy$_3$)$_2$Ru=CHCH=CPh$_2$] (8 mg) were charged in a stainless steel high-pressure reactor (V=225 cm$^{-3}$) under argon atmosphere. The reactor was filled with 170 g of CO$_2$ using a compressor (d=0.76 g·cm$^{-3}$), and the resulting reaction mixture was stirred at 313 K. After 24 h, the CO$_2$ pressure was released over a cooling trap cooled at 233 K. The reactor and the cooling trap were washed with acetone, the combined washings were concentrated, and the residue was purified by column chromatography. The product 10 was obtained in the form of colorless crystals.

Yield: 175 mg (93%)

m.p. 123–124° C.; $^1$H NMR (200 MHz, CDCl$_3$) δ7.73 (d, 2H, J=8.3), 7.32 (d, 2H, J=8.0), 5.67 (t, 2H, J=4.6), 4.12 (t, 4H, J=4.5), 2.43 (s, 3H); IR (film) 3049, 2910, 2854, 1595, 1493, 1476, 1337, 1306, 1162, 1112, 1071, 1018, 1002, 948, 820, 710, 667, 601, 564 cm$^{-1}$.

EXAMPLE 7
Preparation of 1-(4-bromophenyl)cyclopent-3-enole (12)

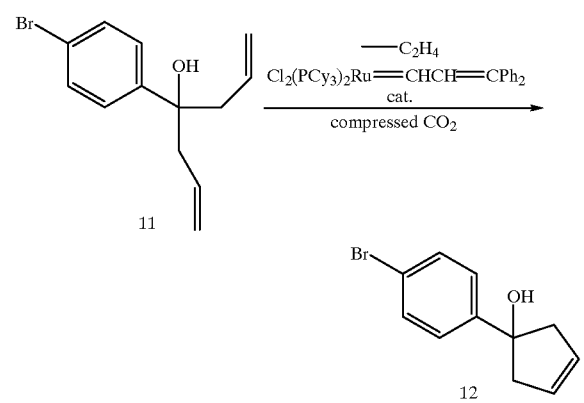

The hydroxydiene 11 (345 mg) and trans-[Cl$_2$(PCy$_3$)$_2$Ru=CHCH=CPh$_2$] (9 mg) were charged in a stainless steel high-pressure reactor (V=225 cm$^{-3}$) under argon atmosphere. The reactor was filled with 177 g of CO$_2$ using a compressor (d=0.79 g·cm$^{-3}$), and the resulting reaction mixture was stirred at 313 K for 18 h. The CO$_2$ pressure was released over three cooling traps cooled at 233 K, and the reactor was washed twice with 170 g each of CO$_2$. After warming up, 87 mg of a colorless solid was obtained from the cooling traps. From the residue remaining in the reactor, another 134 mg of crude product of the same composition could be isolated using acetone. Purification of the combined fractions by column chromatography yielded 12 as a colorless solid.

Yield: 99 mg (32%)

m.p. 77–78° C.; $^1$H NMR (200 MHz, CDCl$_3$) δ7.50–7.34 (m, 4H), 5.85–5.76 (m, 2H), 2.89 (d, 2H, J=16.0 Hz), 2.71 (d, 2H, J=16.0 Hz), 2.15 (s, 1H); IR (KBr) 3331, 3059, 2911, 2846, 1904, 1658, 1614, 1589, 1483, 1426, 1399, .1332, 1306, 1270, 1159, 1073, 1010, 977, 876, 826, 777, 702, 668, 542 cm$^{-1}$.

EXAMPLE 8
Preparation of Epilachnene (14)

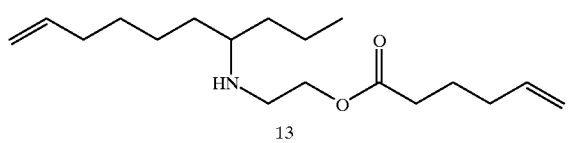

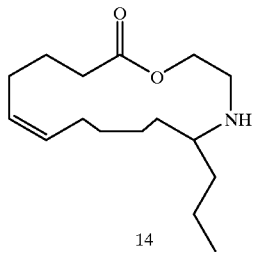

Aminodiene 13 (52 mg, dissolved in 0.5 ml of $CH_2Cl_2$) and trans-$[Cl2(PCy_3)_2Ru=CHCH=CPh_2]$ (7 mg) were charged in a stainless steel high-pressure reactor (V=225 cm³) under argon atmosphere. The reactor was filled with 172 g of $CO_2$ using a compressor (d=0.76 g·cm⁻³), and the resulting reaction mixture was stirred at 313 K for 72 h. The $CO_2$ pressure was released over a cooling trap cooled at 233 K, and the reactor was washed with $Et_2O$. Purification of the combined fractions by column chromatography (alumina, hexane/ethyl acetate 1:1) yielded 44 mg of a slightly yellowish oil which, according to GC analysis, consisted of 74% 14 as a mixture of the double bond-related isomers (cis:trans=30:70) and 22% unreacted 13.

What is claimed is:

1. A process for the preparation of cyclic products by selective olefin metathesis of bifunctional or polyfunctional substrates in the presence of one or more homogeneous or heterogeneous metathesis catalysts in a reaction medium, characterized in that the substrates contain two or more functional groups in the form of substituted or unsubstituted alkene or alkyne moieties, and the reaction medium comprises compressed carbon dioxide, wherein the reaction temperature and the total pressure are mutually adjusted in such a way that the density of the reaction medium is within a range of d=0.4–1.5 g·cm⁻³.

2. The process according to claim 1, wherein the products are carbo- or heterocyclic compounds having ring sizes of ≧5.

3. The process according to claim 2, wherein the products are carbo- or heterocyclic compounds having ring sizes of from 8 to 11.

4. The process according to claim 2, wherein the products are macrocyclic compounds having ring sizes of ≧12.

5. A process for the preparation of polymeric products by selective olefin metathesis of bifunctional or polyfunctional substrates in the presence of a homogeneous or heterogeneous metathesis catalyst in a reaction medium, characterized in that the substrates contain two or more functional groups in the form of substituted or unsubstituted alkene or alkyne moieties, and the reaction medium comprises compressed carbon dioxide, wherein the reaction temperature and the total pressure are mutually adjusted in such a way that the density of the reaction medium is within a range of d=0.2–1.3 g·cm⁻³.

6. The process according to claim 1, wherein metathesisactive metallic compounds which are not inactivated by compressed carbon dioxide are used as catalysts or catalyst precursors.

7. The process according to claim 6, wherein transition metalcarbenes, or transition metallic compounds which form metal-carbenes under the reaction conditions, or transition metal salts in connection with an alkylating agent are used as catalysts or catalyst precursors.

8. The process according to claim 7, wherein compounds of the general types I–IX

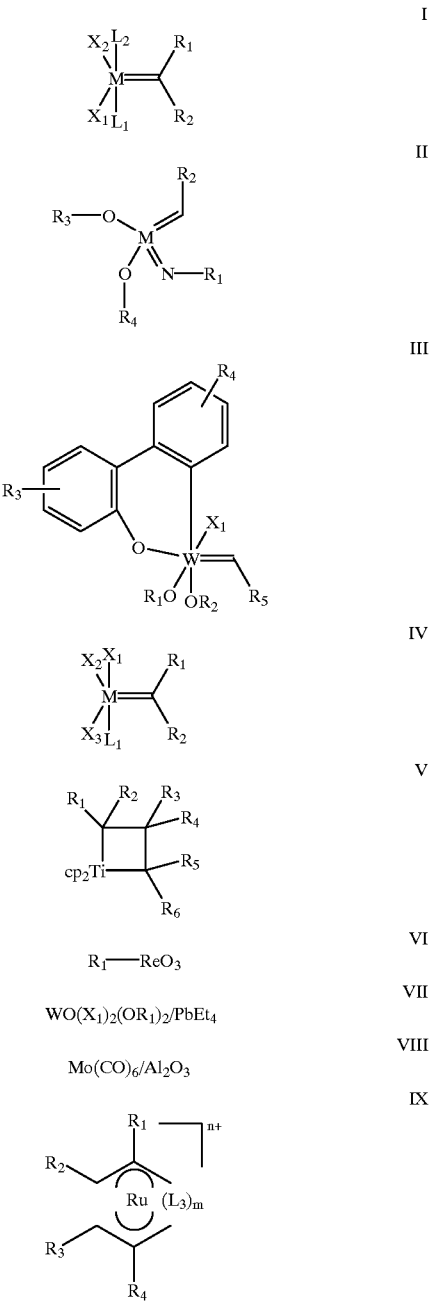

wherein $R_1$–$R_6$ are residues which are independently selected from hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl; each of which may optionally be substituted with $C_1$–$C_{12}$ alkyl $C_1$–$C_{12}$ perfluoroalkyl, halogen, $C_1$–$C_5$ alkoxy or aryl; wherein in cyclic compounds, the residues $R_1$–$R_{10}$ can be linked to one another; $X_1$–$X_3$ are arbitrarily defined anionic ligands;

$L_1$–$L_3$ are neutral ligands; and m, n are integers of from 0 to 6;

are used as catalysts or catalyst precursors.

9. The process according to claim 8, wherein carbene complexes of general type I with $L_1$–$L_2$=$PR_1R_2R_3$ are used as catalysts or catalyst precursors wherein $R_1$–$R_3$ correspond to the definition in claim 8.

10. The process according to claim 1 wherein said bifunctional or polyfunctional substrates are either conformationally preorganized or completely flexible.

11. The process according to claim 1, wherein said bifunctional or polyfunctional substrates contain any number of further groups or heteroatoms compatible with the metathesis reaction in addition to the functional groups which participate in the reaction.

12. The process according to claim 11, wherein said groups or heteroatoms are independently selected from branched or unbranched alkyl residues, aromatic or non-aromatic carbo-cyclic rings, carboxylic acids, esters, ethers, epoxides, silyl ethers, thioethers, thioacetals, anhydrides, imines, silyl enol ethers, ammonium salts, amides, nitriles, perfluoroalkyl groups, gem-dialkyl groups, alkynes, alkenes, halogens, alcohols, ketones, aldehydes, carbamates, carbonates, urethanes, sulfonates, sulfones, sulfonamides, nitro groups, organosilane units, metal centers, oxygen-, nitrogen-, sulfur-, phosphorus-containing heterocycles.

13. The process according to claim 1, wherein said bifunctional or polyfunctional substrates contain one or more primary, secondary or tertiary basic amine units.

14. The process according to claim 1, wherein mixtures of said substrates are reacted which are supplied to the reaction medium in admixture or sequentially.

15. The process according to claim 1, wherein said substrates are wholly or partially in supported form.

16. The process according to claim 1, wherein the products are subjected to a subsequent reaction in the compressed carbon dioxide in an integrated process.

17. The process according to claim 1, wherein the reaction medium additionally contains one or more additives which are independently selected from: water, phosphorus compounds, amines, perfluorinated compounds, Lewis-acidic compounds, metal alkoxides, organic solvents.

18. The process according to claim 1, wherein the products are isolated using the specific solvent properties of compressed carbon dioxide.

19. The process according to claim 1, wherein the metal-containing residues remaining after the separation of the chemical products are reused as catalysts for olefin metatheses.

20. The process according to claims 1, wherein the carbon dioxide used is recycled.

21. The process according to claim 1, wherein the reaction temperature and the total pressure are mutually adjusted in such a way that the density of the reaction medium is within a range of d =0.6–1.5 g·cm$^{-3}$.

22. The process according to claim 5, which is for the preparation of dimeric or oligomeric products.

23. The process according to claim 5, wherein the reaction temperature and the total pressure are mutually adjusted in such a way that the density of the reaction medium is within a range of d=0.2–0.65 g·cm$^{-3}$.

24. The process according to claim 8, wherein compounds of the general types I–IX

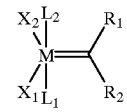

I

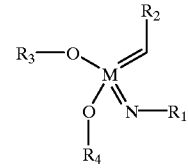

II

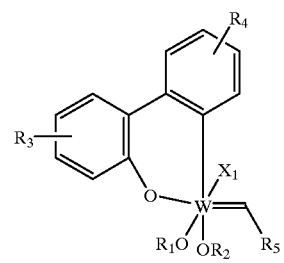

III

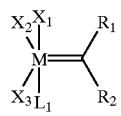

IV

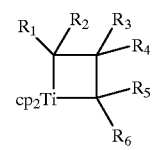

V

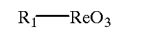

VI

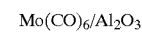

VII

Mo(CO)$_6$/Al$_2$O$_3$

VIII

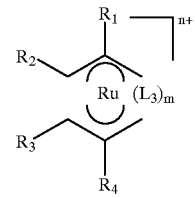

IX wherein $R_1$–$R_6$ are residues which are independently selected from hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl; each of which may optionally be substituted with $C_1$–$C_{12}$ alkyl, $C_1$–$C_{12}$ perfluoroalkyl, halogen, $C_1$–$C_5$ alkoxy or aryl; wherein in cyclic compounds, the residues $R_1$–$R_{10}$ can be linked to one another; $X_1$–$X_3$ are arbitrarily defined anionic ligands which are independently selected from F$^-$, Cl$^-$, Br$^-$, I$^-$, CN$^-$, SCN$^-$, $R_1O^-$, $R_1R_2N^-$, ($R_1$–$R_5$)-allyl$^-$, ($R_1$–$R_5$)- cyclopenadienyl⁻, the residues $R_1$–$R_5$ corresponding to the above definition;

$L_1$–$L_3$ are neutral ligands which are independently selected from CO, $CO_2$, $R_1NCO$, $R_1R_2C{=}CR_3R_4$, $R_1C{\equiv}CR_2$, $R_1R_2C{=}NR_3$, $R_1C{\equiv}N$, $R_1OR_2$, $R_1SR_2$, $NR_1R_2R_3$, $PR_1R_2R_3$, $AsR_1R_2R_3$, $SbR_1R_2R_3$; and m, n are integers of from 0 to 6;

are used as catalysts or catalyst precursors.

25. The process according to claim 9, wherein carbene complexes of general type I with $L_1$–$L_2$ =$PR_1R_2R_3$ are used as catalysts or catalyst precursors wherein $R_1$–$R_3$ represent aryl or alkyl or cycloalkyl residues.

26. The process according to claim 25, wherein said alkyl is a secondary alkyl residue.

27. The process according to claim 8, wherein carbene complexes of general type II with $R_1$=aryl and $R_2$–$R_4$= $C_1$–$C_{20}$ alkyl, each of which may optionally be substituted with $C_1$–$C_{12}$ alkyl, $C_1$–$C_{12}$ perfluoroalkyl, aryl, or halogen, are used as catalysts or catalyst precursors.

28. The process according to claim 17, wherein said organic solvents are selected from dichloromethane, trichloromethane, tetrachloromethane, 1,2-dichloroethane, trichloroethane, benzene, toluene, xylene, cumene, hexane, cyclohexane, halobenzenes, tetrahydrofuran, tert-butyl methyl ether, diethyl ether, dimethoxyethane, dimethylforamide, ethyl acetoacetate, acetone, dimethylcarbonate, alcohols.

29. The process according to claim 4, wherein the products are selected from pentadecanolide, dodecanedioic acid ethylene ester, cycloheptadec-9-en-1-one, 3-methyl-cyclopentadecan-1-one, cyclopentadecanone, 3-methyl-cyclopentadec-5-en-1 -one and epothilone and macrocyclic homologs of such products having ring sizes $\geqq 12$.

* * * * *